United States Patent
Stirnemann

(10) Patent No.: US 6,837,857 B2
(45) Date of Patent: Jan. 4, 2005

(54) METHOD FOR THE RECORDING OF ACOUSTIC PARAMETERS FOR THE CUSTOMIZATION OF HEARING AIDS

(75) Inventor: Alfred Stirnemann, Zollikon (CH)

(73) Assignee: Phonak AG, Stafa (CH)

( * ) Notice: Subject to any disclaimer, the term of this patent is extended or adjusted under 35 U.S.C. 154(b) by 214 days.

(21) Appl. No.: 10/207,281

(22) Filed: Jul. 29, 2002

(65) Prior Publication Data

US 2004/0019294 A1 Jan. 29, 2004

(51) Int. Cl.⁷ .................................................. A61B 5/00
(52) U.S. Cl. .................................................... 600/559
(58) Field of Search ........................... 600/559; 381/1, 381/309, 310; 73/585, 589

(56) References Cited

U.S. PATENT DOCUMENTS

| 4,289,143 A | | 9/1981 | Canavesio et al. |
| 4,809,708 A | | 3/1989 | Geisler et al. |
| 5,526,819 A | | 6/1996 | Lonsbury et al. |
| 5,792,072 A | * | 8/1998 | Keefe .......................... 600/559 |
| 6,118,875 A | * | 9/2000 | M.o slashed.ller et al. ..... 381/1 |

* cited by examiner

*Primary Examiner*—Max F. Hindenburg
*Assistant Examiner*—Brian Szmal
(74) *Attorney, Agent, or Firm*—Pearne & Gordon LLP

(57) ABSTRACT

Acoustic parameters of an ear are recorded by measuring the impedance of the ear canal. A first pressure microphone measures the sonic pressure. A second pressure microphone measures the sonic pressure through a calibrated acoustic resistance. The sound energy flux is determined by the difference between the measured sonic pressures. The impedance is calculated from these results.

10 Claims, 2 Drawing Sheets

Figure 1:
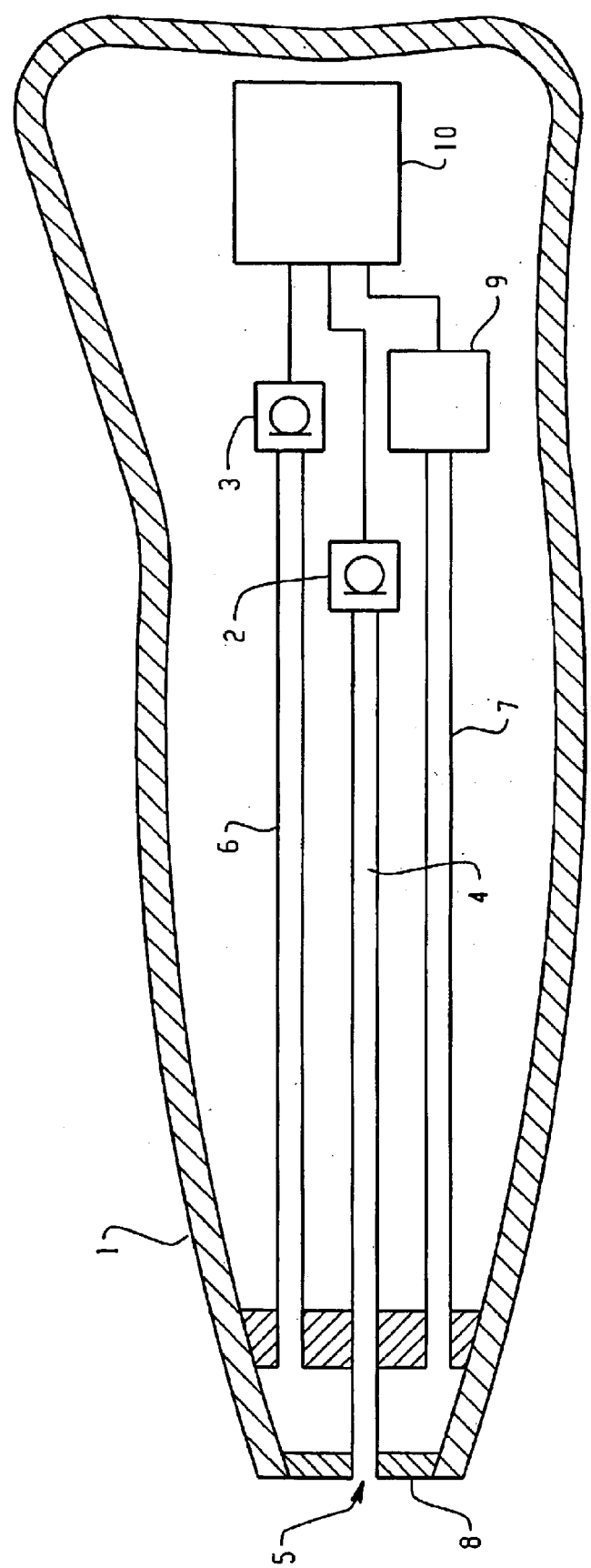

METHOD FOR THE RECORDING OF ACOUSTIC PARAMETERS FOR THE CUSTOMIZATION OF HEARING AIDS

BACKGROUND OF INVENTION

The ear and the ear canal as a part of an organism are having individual acoustic qualities. The adaptation of hearing aids to these individual acoustic conditions is very complicated, takes great pain and is full of many uncertainties. After the insertion of a hearing aid or hearing device into the ear canal, a lot of different factors have important influence on the acoustic qualities, such as the remaining volume in the ear canal, the distance to the eardrum, the impedance of the eardrum, the transmission qualities of the inner ear, the fitting of the hearing aids, e.g. an otoplastique etc.

Acoustic impedance measuring are commonly carried out practically only for diagnostic purposes, known as Tympanometry, measuring of reflectance, measuring of compliance etc. Such diagnostic measurements will be carried out only at few frequencies, whereby varying the static pressure as a parameter in the ear canal. Most frequently the measurement will be carried out by a stimulation by means of a listener and the receiving of the stimulated sound by means of a microphone, which is coupled either directly or through adapters with the ear canal. The evaluation of this measurement is carried out via external, extensive electronics, most frequently with computer support, and the results are of interest only for diagnostic purposes. Due to this effort and the respective high costs, those proceedings are not suitable for use for the customization of hearing aids.

The measuring of the effective sound pressure in the ear canal takes a great effort and is frequently carried out by means of hose probes which are very sensitive with respect to its final position and even influences the sound system of the ear canal. Particularly measuring at higher frequencies are full of large uncertainties and error sources and therefore the results do not ensure any optimal customizations for the hearing aids.

OBJECTS OF THE PRESENT INVENTION

One object of the present invention is to provide a method for a simple and reliable customization of hearing aids without the need of complicate and cost or time intensive separate or additional measurements.

A further object of the present invention is to provide a measuring device for simple and reliable customization of hearing aids.

SUMMARY OF INVENTION

In a preferred embodiment of the invention, by the determination of the impedance about an acoustic reference resistance neither the frequency response of the acoustic receiver nor the signal frequency has an influence on the measuring result. Advantageously a broadband measuring signal will be retrieved which can be consulted or used directly for the evaluation of the acoustic parameters.

In a further embodiment of the present invention, an acoustic resistance out of porous sinter bronze is used, preferably arranged concentrically around a channel of the first pressure microphone.

In a further embodiment of the present invention, the measuring will be performed by means of pressure microphones arranged in a hearing aid shell, whereby the hearing aid shell is introduced into the ear canal before starting the measuring.

In a further embodiment of the present invention, the evaluation of the signals is made by electronic components, preferably a programmable microchip, arranged in the hearing aid shell.

In a further embodiment of the present invention, curve fit proceedings will be implemented onto the measuring results, to calculate or estimate one or more of the following parameters:

Impedance; e.g. the complex impedance in a frequency range up to approx. 10 kHz for optimal acoustic customization of hearing aids.

Effective distance of the hearing aid outlet to the eardrum.

Compliance of the rest volume of the ear canal, i.e. the rest volume remaining after the insertion of the shell of the hearing aid.

Overall compliance at deep frequencies.

Individual transitional function of the inner ear.

Effect of leaks; i.e. the effect of vent and leaks caused by the positioning of the shell of the hearing aid within the ear canal.

In a further embodiment of the present invention, the measuring is made under variable, adjustable static pressure in the ear canal.

In a further embodiment of the present invention, the static pressure is adjusted over an additional static pressure line for the ear canal.

A preferred embodiment of the present invention defines a measuring device for performing the method of the recording of acoustic parameters of the ear by measuring the impedance of the ear canal by measuring the sonic pressure by a first pressure microphone and by determining the sonic by the difference of the measured sonic pressure in relation to the sonic pressure measured by a second pressure microphone through a calibrated acoustic resistance, and by finally calculating the impedance out of those two results, with a probe to be at least partly introduced into the ear canal, whereby at least two microphones are arranged within the probe, and whereby at least for one of the microphones an acoustic resistance is pre-connected.

In a further embodiment of the present invention, the acoustic resistance is formed by a porous sinter bronze.

In a further embodiment of the present invention, the measuring device is arranged within the shell of a hearing aid, with the shape of said shell preferably adapted to the ear canal, and with an evaluation electronics situated within the shell which is connected to microphones of the measuring device.

A large advantage of the present method is to be seen by the preferential arrangement of the measuring organs, i.e. the microphones and the acoustic resistance, incorporated in the hearing aids itself, so that no additional measuring facilities are necessary to perform the measurement. The inaccuracies of the common measuring due to the different conditions in the ear canal with resp. without the hearing aid inserted into the ear canal are therefore advantageously avoided.

No large additional effort has to be taken even for the evaluation facilities, as the common miniaturized hearing aids comprises already digital techniques and components.

Another advantage can further be seen into it that the measuring simply can be repeated periodically and that therefore the hearing aid can periodically be adapted to any changed conditions of the ear canal. It is conceivable that the customization can be run through the electronics of the hearing aid itself automatically and doesn't cause any manual intervention by the user or a specialist.

By the procedure according to the present invention an optimal acoustic customization of the hearing aids can advantageously be ensured, eventually automatically.

DRAWINGS

Figure 2:
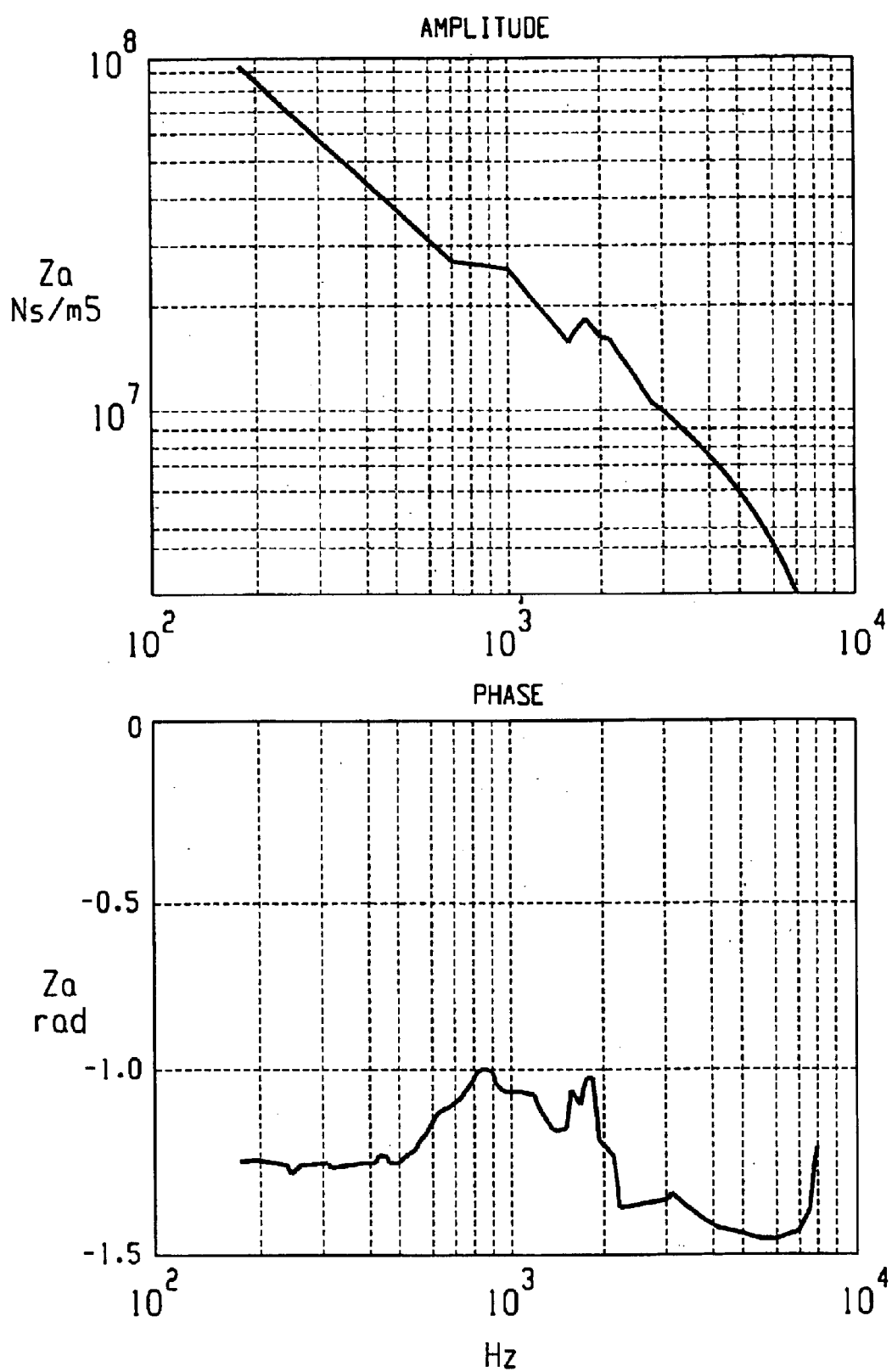

These and other objects and advantages of the present invention will become apparent from the following detailed description of the accompanying drawings in which:

FIG. 1 schematically shows the longitudinal section of an hearing aid according the present invention; and FIG. 2 the measured curve of the impedance of an ear shell in amplitude and phase.

DETAILED DESCRIPTION

In the drawings, FIG. 1 shows the longitudinal section of a preferably miniaturized hearing aid. The front part of the shell with the shape of the ear canal will be slid into ear canal (not represented in the figure). At least two microphones 2 and 3 are arranged within the shell, The first microphone 2 is connected to the opening 5 of the shell 1 over an open channel 4 This microphone 2 serves for the measuring of the effective sound pressure in the ear canal. The second microphone 3 is also connected to the opening 5 over a channel 6 in which an acoustic resistance 8 is arranged between the outside of the opening 5 and the channel 6. In the case in hand the acoustic resistance 8 consists preferably of a circle disk of porous sinter bronze with a defined, calibrated acoustic resistance value Ra.

A listener 9 delivers the amplified outside sound or an artificial, broadband measuring signal to the channel 7 which is brought together with the channel 6 before the acoustic resistance 8.

The two microphones 2 and 3 are connected with an evaluation electronics 10 in form of a chip, which calculates the impedance Za according to the formula described below.

$$Za = Ra * p2/(p1-p2)$$

P2 is the effective sound pressure of the ear canal (between hearing aid and eardrum) to be measured and P1 is the effective sound pressure before the acoustic reference resistance Ra. The effective sound pressure is measured directly by means of the respective microphones 2 (effective sound pressure P2) and microphones 3 (effective sound pressure P1), while the resistance value Ra is determined by a calibration of the resistance 8 due to known material qualities.

As the sound energy flux is determined over the pressure difference P1–P2, the determination of the impedance Za can be carried out advantageously frequency-independently.

The result of such a measuring or calculation of the impedance Za of a real ear shell according to invention is represented in amplitude and phase as an example in FIG. 2 of the drawings.

By the use of the technology used in the hearing aid technique, a broadband measuring result can be attained in which the microphone signals can be evaluated directly and used for the calculation of the impedance by using digital computer chips.

By the application of curve fit procedures the derived results can be used for the identification of a number of parameters of the inner ear and have, for example, the following qualities to calculate or to assess at least:

Complex impedance in a frequency domain up to approx. 10 kHz for optimal acoustic customization of hearing aids, Determination of the effective distance between outlet of the hearing aid and eardrum.

Compliance rest volume of the ear canal.

Overall compliance at deep frequencies with respect to the rest volume, the eardrum and the middle ear.

Individual transitional functions of the inner ear.

Effect of vent and leaks with respect to the positioning of the shell of the hearing aid.

Connections for static pressure changes can further be provided to carry out appropriate tests according the teaching of Tympanometry. Note functions also can be scheduled which records certain parameters such as the note of stimulated otoacoustic issues.

What is claimed is:

1. Method of measuring an impedance of an ear canal comprising the steps of:

measuring a first sonic pressure with a first pressure microphone;

determining a sound energy flux by the difference of the measured first sonic pressure in relation to a second sonic pressure measured with a second pressure microphone through a calibrated acoustic resistance; and calculating the impedance from said first and second sonic pressures.

2. Method according to claim 1 wherein the calibrated acoustic resistance comprises porous sinter bronze arranged concentrically around a channel of the first pressure microphone.

3. Method according to claim 1, wherein the step of measuring is performed by pressure microphones arranged in a hearing aid shell, and wherein the hearing aid shell is introduced into the ear canal before starting the step of measuring.

4. Method according to claim 3 wherein the step of calculating comprises evaluation of signals from said first and second pressure microphones by electronic components arranged in the hearing aid shell.

5. Method according to claim 1 further comprising the step of implementing curve fit proceedings onto the measuring results, to calculate or estimate the following parameters:

impedance, and/or effective distance of a hearing aid outlet to an eardrum, and/or compliance of a rest volume of the ear canal, and/or overall compliance at deep frequencies, and/or individual transitional function of an inner ear, and/or effect of leaks.

6. Method according to claim 1 wherein the measuring is made under variable, adjustable static pressure in the ear canal.

7. Method according claim 6 wherein the static pressure is adjusted over an additional static pressure line for the ear canal.

8. A measuring device for performing a method of measuring an impedance of an ear canal comprising:

a first pressure microphone measuring first sonic pressure;

a second pressure microphone for measuring a second sonic pressure through a calibrated acoustic resistance;

means for determining a sound energy flux by the difference of the measured first sonic pressure in relation to the measured second sonic pressure; means for calculating the impedance from said first and second sonic pressures; and a probe adapted to be at least partly introduced into the ear canal, wherein said first and second microphones are arranged within the probe, and wherein an acoustic resistance is pre-connected to at least one of said first and second microphones.

9. Measuring device according to claim 8 wherein the calibrated acoustic resistance comprises a porous sinter bronze.

10. Measuring device according to claim 8 arranged within a shell of a hearing aid adapted to a shape of the ear canal, and comprising evaluation electronics arranged within the shell and connected to said first and second microphones of the measuring device.

* * * * *

UNITED STATES PATENT AND TRADEMARK OFFICE
CERTIFICATE OF CORRECTION

PATENT NO. : 6,837,857 B2
DATED : January 4, 2005
INVENTOR(S) : Alfred Stirnemann It is certified that error appears in the above-identified patent and that said Letters Patent is hereby corrected as shown below:

<u>Column 3,</u>
Line 16, please delete "," and insert therefor -- . --.
Line 18, after the "4", please insert therefor -- . --.

<u>Column 4,</u>
Line 4, after the word "according", please insert therefor -- to --.
Line 54, after the word "measuring", please insert therefor -- a --.

Signed and Sealed this

Eighteenth Day of October, 2005

JON W. DUDAS
*Director of the United States Patent and Trademark Office*